US009168382B2

(12) United States Patent
Shuros et al.

(10) Patent No.: US 9,168,382 B2
(45) Date of Patent: Oct. 27, 2015

(54) METHOD AND APPARATUS FOR SELECTIVE HIS BUNDLE PACING

(71) Applicant: Cardiac Pacemakers, Inc., St. Paul, MN (US)

(72) Inventors: Allan C. Shuros, St.Paul, MN (US); Jiang Ding, Shoreview, MN (US); Barun Maskara, Blaine, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 57 days.

(21) Appl. No.: 14/043,523

(22) Filed: Oct. 1, 2013

(65) Prior Publication Data

US 2014/0107724 A1    Apr. 17, 2014

Related U.S. Application Data

(60) Provisional application No. 61/712,403, filed on Oct. 11, 2012.

(51) Int. Cl.
*A61N 1/37* (2006.01)
*A61B 5/053* (2006.01)

(52) U.S. Cl.
CPC ............ *A61N 1/3712* (2013.01); *A61B 5/0538* (2013.01); *A61N 1/371* (2013.01)

(58) Field of Classification Search
CPC ..... A61B 5/0538; A61N 1/371; A61N 1/3712
USPC .............................................. 607/11, 28, 122
See application file for complete search history.

(56) References Cited

U.S. PATENT DOCUMENTS

| | | | |
|---|---|---|---|
| 4,686,987 A | 8/1987 | Salo et al. | |
| 4,773,401 A | 9/1988 | Citak et al. | |
| 5,174,286 A | 12/1992 | Chirife | |
| 5,800,467 A | 9/1998 | Park et al. | |
| 5,843,137 A * | 12/1998 | Condie et al. | 607/28 |
| 6,522,924 B1 * | 2/2003 | Meier | 607/28 |
| 6,609,027 B2 * | 8/2003 | Kroll et al. | 607/9 |
| 7,027,863 B1 | 4/2006 | Prutchi et al. | |
| 7,027,876 B2 * | 4/2006 | Casavant et al. | 607/126 |
| 7,778,696 B2 * | 8/2010 | Sathaye | 600/509 |
| 8,812,106 B2 * | 8/2014 | Ortega et al. | 607/9 |
| 2007/0016261 A1 | 1/2007 | Dong et al. | |
| 2008/0021336 A1 | 1/2008 | Dobak | |
| 2009/0036950 A1 * | 2/2009 | Armstrong et al. | 607/45 |
| 2011/0264158 A1 * | 10/2011 | Dong et al. | 607/9 |
| 2012/0239106 A1 * | 9/2012 | Maskara et al. | 607/28 |

OTHER PUBLICATIONS

Chirife, Raul, et al., "Feasibility of measuring relative right ventricular volumes and ejection fraction with implantable rhythm control devices", Pacing Clin Electrophysiol., 16(8) Aug. 1993, 1673-83.
Maskara, Barun, et al., "HIS Capture Verification Using Electro-Mechanical Delay", U.S. Appl. No. 61/452,412, filed Mar. 14, 2011.
Maskara, Barun, et al., "HIS Capture Verification Using Electro-Mechanical Delay", U.S. Appl. No. 13/404,814, filed Feb. 24, 2012.

* cited by examiner

*Primary Examiner* — William Levicky
(74) *Attorney, Agent, or Firm* — Schwegman Lundberg & Woessner, P.A.

(57) ABSTRACT

A cardiac rhythm management system provides for cardiac pacing that is delivered to a target portion of conductive tissue in a heart, such as the His bundle. In various embodiments, the system is configured to verify capture of the target portion and provide for selective pacing of the target portion. In various embodiments, the system is configured to detect responses of the target portion and adjacent myocardial tissue to delivery of pacing pulses and use an outcome of the detection to verify selective capture of the target portion (i.e., without directly exciting the adjacent myocardial tissue.

20 Claims, 7 Drawing Sheets

METHOD AND APPARATUS FOR SELECTIVE HIS BUNDLE PACING

CLAIM OF PRIORITY

This application claims the benefit of priority under 35 U.S.C. §119(e) of U.S. Provisional Patent Application Ser. No. 61/712,403, filed on Oct. 11, 2012, which is herein incorporated by reference in its entirety.

TECHNICAL FIELD

This document relates generally to cardiac rhythm management systems and more particularly to a cardiac pacing system that provides for selective pacing of a target portion of cardiac conductive tissue, such as a His bundle.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, that propagate through an electrical conduction system to various regions of the heart to excite the myocardial tissues of the cardiac muscles. For example, the action potentials originated from the SA node propagate through the atrioventricular (AV) node that is between RA and RV, the His bundle (also known as Bundle of His), and purkinje fibers to reach the ventricular myocardial tissues, resulting in contraction activities of the ventricles.

Coordinated delays in the propagations of the action potentials in a normal electrical conduction system cause the various portions of the heart to contract in synchrony to result in efficient pumping functions. A blocked or otherwise abnormal electrical conduction and/or deteriorated myocardial tissue cause dyssynchronous contraction of the heart, resulting in poor hemodynamic performance, including a diminished blood supply to the heart and the rest of the body. For example, an abnormal delay in the transmission of the action potentials in the His bundle can cause irregular or dyssynchronous contractions of the ventricles, resulting in an abnormal rhythm of the heart. In such events of cardiac malfunctioning, an artificial cardiac pacing system may be used. The artificial cardiac pacing system can provide electrical stimulations to one or more portions of the heart such as to restore normal functioning of the heart to a certain extent. However, the artificial cardiac pacing can result in dyssynchronous myocardial contraction patterns when not being used adequately. For example, His Bundle pacing may cause dyssynchronous myocardial contraction patterns when the electrical stimulation activates not only the His Bundle but also the adjacent myocardial tissue, an undesirable event referred to as non-selective His Bundle pacing. Therefore, there is a need for configuring cardiac pacing system for achieving the desirable therapeutic effects while reducing or eliminating unintended effects such as activation of non-targeted portions of the heart.

SUMMARY

A cardiac rhythm management system provides for cardiac pacing that is delivered to a target portion of conductive tissue in a heart, such as the His bundle. In various embodiments, the system is configured to verify capture of the target portion and provide for selective pacing of the target portion. In various embodiments, the system is configured to detect responses of the target portion and adjacent myocardial tissue to delivery of pacing pulses and use an outcome of the detection to verify selective capture of the target portion (i.e., without directly exciting the adjacent myocardial tissue.

In one embodiment, a pacing system can include a pacing output circuit, a sensing circuit, and a control circuit. The pacing output circuit delivers pacing pulses to a target portion of the conductive tissue in a heart. The sensing circuit senses one or more signals indicative of one or more responses of the heart to the delivery of each pulse of the pacing pulses. The control circuit can be configured to control the delivery of the pacing pulses using pacing parameters and includes a capture verification circuit. The capture verification circuit is configured to perform a selective capture verification that includes detection of conductive tissue responses and myocardial responses using the sensed one or more signals. The conductive tissue responses are each representative of excitation of the target portion of the conductive tissue directly resulting from the delivery of the each pulse. The myocardial responses are each representative of excitation of portions of the myocardial tissue directly resulting from the delivery of the each pulse. A specific example of the target portion of the conduction tissue in the heart is the His bundle.

In one embodiment, a method for operating an implantable cardiac pacemaker for His bundle pacing is provided. Pacing pulses are delivered to a target portion of the conduction tissue in a heart from the implantable cardiac pacemaker. The delivery of the pacing pulses is controlled using pacing parameters. One or more signals indicative of one or more responses of the heart to the delivery of each pulse of the pacing pulses are sensed. A selective capture verification is performed. The selective capture verification includes detecting conductive tissue responses using a first signal of the sensed one or more signals and detecting myocardial responses using a second signal of the sensed one or more signals. The conductive tissue responses are each representative of excitation of the target portion of the conduction tissue directly resulting from the delivery of the each pulse. The myocardial responses are each representative of excitation of portions of the myocardial tissue directly resulting from the delivery of the each pulse. A specific example of the target portion of the conduction tissue in the heart is the His bundle.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals may describe substantially similar components throughout the several views. The drawings illustrate gener

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses, among other things, a cardiac rhythm management system including a cardiac pacemaker that can be configured to provide selective pacing of cardiac conductive tissue without directly exciting adjacent myocardial tissue. One example of such selective pacing includes selective His bundle pacing. In various embodiments, the present system is configured to detect responses of the His bundle and adjacent myocardial tissue to delivery of pacing pulses. In various embodiments, the present system adjusts one or more parameters controlling the delivery of the pacing pulses such that the delivered pacing pulses excite the His bundle without exciting the adjacent myocardial tissue.

While selective His bundle pacing is specifically discussed in this document, in various embodiments, the present cardiac rhythm management system and method can be applied to provide selective pacing of other cardiac conductive tissue without directly exciting the adjacent working myocardium. Examples of the other conductive tissue as targets for the selective pacing include, but are not limited to, the right or left bundle branches or fascicles.

Figure 1:
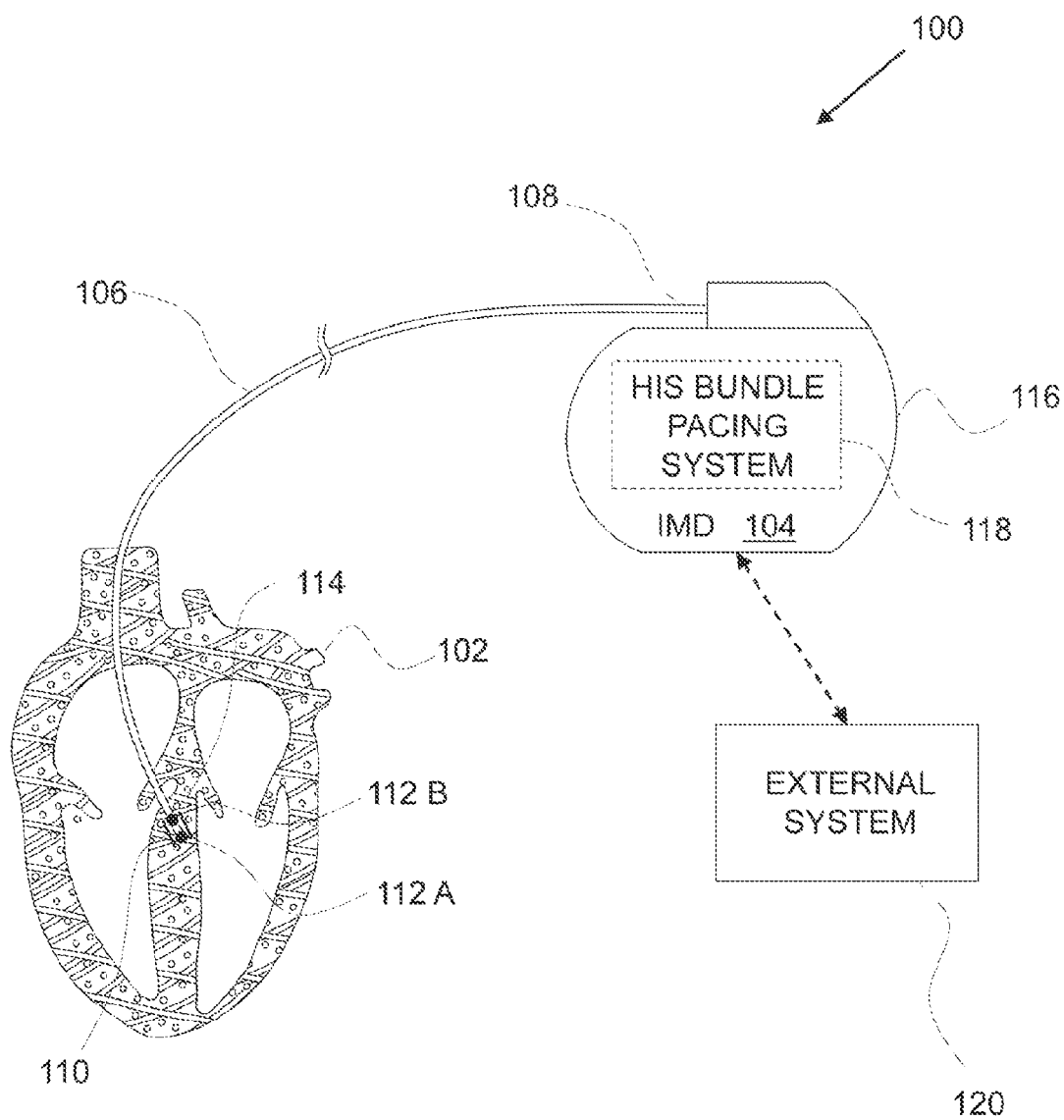
- FIG. 1 is a schematic diagram illustrating an embodiment of portions of a cardiac rhythm management (CRM) system and the environment in which the system can be used.

FIG. 1 is a schematic diagram illustrating an embodiment of portions of a cardiac rhythm management (CRM) system 100 and an environment in which the CRM system 100 can be used. The CRM system 100 can be coupled to a patient's heart 102 to treat one or more abnormalities associated with the functioning of the heart 102. In the illustrated embodiment, the CRM system 100 includes an implantable medical device (IMD) 104 and a lead 106. The lead 106 provides for an electrical interface between the IMD 104 and the heart 102, and includes a proximal end 108 and a distal end 110. The proximal end 108 is configured to be connected to the IMD 104. The distal end 110 includes one or more electrodes, such as 112A and 112B, and can be placed in the heart 102 as shown in FIG. 1. The one or more electrodes are referred to as electrodes 112 for simplicity of the description.

In one embodiment, the IMD 104 can be configured to monitor health of the heart 102 and determine one or more abnormalities associated with the heart 102. The IMD 104 can also take a necessary action, such as stimulating one or more portions of the heart 102 through the electrodes 112, to treat the one or more abnormalities. The distal end 110 of the lead 106 can be configured to be placed in or on His bundle 114 of the heart 102 and the IMD 104 is configured to stimulate the His bundle 114 to treat the one or more abnormalities of the heart 102. In various embodiments, the IMD 104 includes a cardiac pacemaker suitable for His bundle pacing. In various embodiments, IMD 104 also includes one or more other monitoring and/or therapeutic devices including, but not limited to, a defibrillator, a cardioverter, a cardiac resynchronization therapy device, a neurostimulator, a drug delivery device, and a cardiac condition monitor.

The IMD 104 includes a hermetically sealed housing 116 that contains a His bundle pacing system 118. In various embodiments, the His bundle pacing system 118 is configured to verify selective His bundle capture and perform selective pacing of the His bundle 114. The His bundle pacing system 118 is configured to transmit pacing pulses to the His bundle 114 via an electrode system, such as provided by the lead 106. The electrode system has a configuration that can be selected from multiple available electrode configurations based on electrodes 112 and other electrodes of the system 100. For example, the available electrode configurations for pacing the His bundle 114 can include a unipolar electrode configuration and a bipolar electrode configuration. The unipolar electrode configuration can include an electrode of the electrodes 112 and the housing 116 functioning as another electrode. The bipolar electrode can include the electrodes 112A and 112B. In addition to the electrodes 112 and the housing 116, the system 100 can also include other electrodes to allow for selection of target sites to which the pacing pulses are delivered. In one embodiment, the electrode configuration for pacing the His bundle 114 can be programmed by selecting electrodes from the electrodes available in the system 100.

The IMD 104 is configured to wirelessly communicate with an external system 120. The external system 120 is used for remotely instructing the IMD 104 to perform various functions including a selective His bundle capture verification. For example, a user can issue a command to the IMD 104 through a user interface of the external system 120 to initiate the selective His bundle capture verification. The external system 120 can also be used to instruct the IMD 104 to select an appropriate electrode configuration depending on the nature of the signal to be sensed and/or the therapy to be delivered. The external system 120 also receives information from the IMD 104 such as to monitor conditions of the patient and functioning of the IMD 104. In various embodiments, the external system 120 displays received information to the user to allow for analysis of conditions of the patient and performance of the MID 104.

Figure 2:
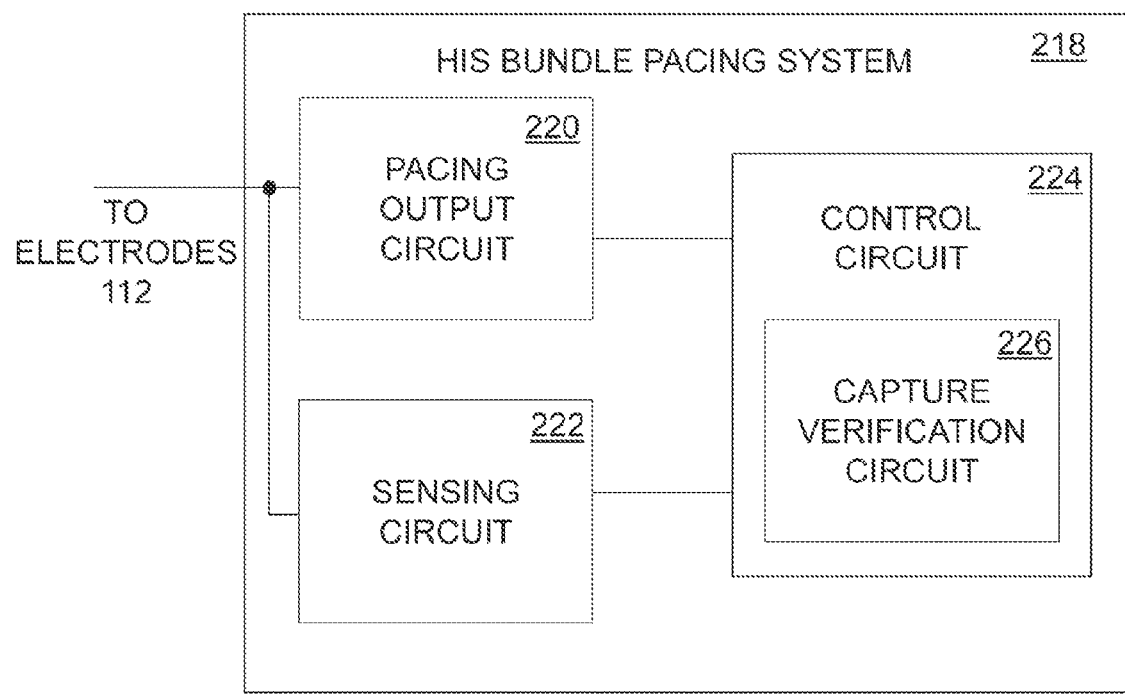
FIG. 2 is a block diagram illustrating an embodiment of a His bundle pacing system.

FIG. 2 is a block diagram illustrating an embodiment of portions of a circuit of a His bundle pacing system 218. The His bundle pacing system 218 represents an embodiment of His bundle pacing system 118 and can include a pacing output circuit 220, a sensing circuit 222, and a control circuit 224. The pacing output circuit 220 generates one or more pacing pulses for delivery to one or more portions of the heart 102. In various embodiments, pacing output circuit 220 is configured to generate one or more pacing pulses that allow for performance of the selective His bundle pacing. In this document, the "selective His bundle pacing" refers to delivering cardiac pacing pulses to the His bundle 114 with only the His bundle 114 being excited (depolarized) by the pacing pulses and without substantial unintended and undesirable excitation of other portions of the heart 102, particularly myocardial tissue adjacent to the His bundle 114, in direct response to the pacing pulses. The "non-selective His bundle pacing" refers to delivering cardiac pacing pulses to the His bundle 114 with the His bundle 114 as well as other portions of the heart 102, particularly myocardial tissue adjacent to the His bundle 114, being excited (depolarized) directly by the pacing pulses. More generally, "selective pacing" refers to delivering cardiac pacing pulses to an intended target (e.g., a portion of the electrical conduction system of the heart 102) with only the targeted tissue being excited (depolarized) by the pacing pulses and without substantial unintended and undesirable excitation of other portions of the heart 102, particularly myocardial tissue adjacent to the targeted tissue, in direct response to the pacing pulses. The "non-selective pacing" refers to delivering cardiac pacing pulses to the intended target with the targeted tissue as well as other portions of the heart 102, particularly myocardial tissue adjacent to the targeted tissue, being excited (depolarized) directly by the pacing pulses.

In various embodiments, the His bundle pacing system 218 can also provide for selective pacing to a target portion of the conductive tissue of the heart 102 other than the His bundle 114 (e.g., another branch of the electrical conduction system of the heart 102). The pacing output circuit 220 delivers pacing pulses to the target portion of the conductive tissue. The sensing circuit 222 senses one or more signals indicative of one or more responses of the heart to the delivery of each pulse of the pacing pulses. The control circuit 224 controls the delivery of the pacing pulses using pacing parameters and includes a capture verification circuit configured to perform a selective capture verification including detection of conductive tissue responses and myocardial responses using the sensed one or more signals. The conductive tissue responses are each representative of excitation of the target portion of the conductive tissue directly resulting from the delivery of the each pulse. The myocardial responses are each representative of excitation of portions of the myocardial tissue directly resulting from the delivery of the each pulse. In other words, the His bundle 114 is a specific example of the target portion of the conductive tissue of the heart 102 used in this document to illustrate the present subject matter, which generally applies to verification of selective pacing of any target portion of the cardiac conductive tissue such as any branch of the electrical conduction system of the heart. In various embodiments, the His bundle pacing system 218 can be programmed with various parameters selected or otherwise suitable for the target portion of the conductive tissue, which can be the His bundle 114 or any other branch of the electrical conduction system of the heart 102. Upon reading and understanding this document, those skill in the art will understand how such various parameters can be determined for the His bundle 114 or another branch of the electrical conduction system of the heart 102.

In response to the delivery of a pacing pulse to a region of the heart 102, a cardiac response from that region can be detected to indicate capture, or excitation of the region. In various embodiments, one or more signals can be sensed to allow for identification of a capture pattern of the heart 102. The selective His bundle pacing and the non-selective His bundle pacing are known to be associated with different capture patterns as represented by one or more sensed signals. Thus, in various embodiments, different capture patterns can be determined to differentiate the selective His bundle pacing from the non-selective His bundle pacing.

The sensing circuit 222 senses one or more signals indicative of the cardiac response of the heart 102 to the delivery of each pacing pulse. Examples of the one or more signals include electrogram signal, impedance signal, and other signals indicative of the capture pattern of interest. In various embodiments, the sensing circuit 222 can sense signals indicative of cardiac responses representing the capture pattern of the selective His bundle pacing. In various embodiments, the sensing circuit 222 can sense signals indicative of cardiac responses representing the capture pattern of the non-selective His bundle pacing. In one embodiment, the sensing circuit 222 can be configured to sense the signal using the same one or more electrodes 112 used for delivering the pacing pulses.

The control circuit 224 is configured to analyze the one or more signals sensed by the sensing circuit 222 and, using an outcome of the analysis, control the delivery of the pacing pulses to perform the selective His bundle pacing. In the illustrated embodiment, the control circuit 224 includes a capture verification circuit 226 that is configured to perform the selective His bundle capture verification using the one or more sensed signals. The selective His bundle capture verification provides for recognition of whether cardiac responses as indicated by the sensed one or more signals are His bundle responses or myocardial responses. Each His bundle response is representative of excitation of the His bundle 114 directly resulting from the delivery of the each pacing pulse. Each myocardial response is representative of unintentional excitation of the myocardial tissue directly resulting from the delivery of the each pacing pulse. In various embodiments, the myocardial response includes a mechanical response of the heart that directly results from the delivery of the each pacing pulse. While detection of this mechanical response using impedance is discussed as a specific example in this document, in various embodiments, the myocardial response can be detected using any one or more sensed signals indicative of this mechanical response.

In various embodiments, the control circuit 224 can be programmed to adjust one or more pacing parameters controlling the delivery of the pacing pulses using an outcome of the selective His bundle capture verification performed by the capture verification circuit 226. For example, in response to the outcome of the selective His bundle capture verification indicating non-selective His bundle pacing, the control circuit 224 adjusts the one or more pacing parameters until the His bundle responses are detected while the myocardial responses are not detected. Detection of the myocardial responses during the selective His bundle capture verification indicates that the non-selective His bundle pacing has occurred. When the His bundle responses and the myocardial responses are both detected, the control circuit 224 adjusts the one or more pacing parameters such that only the His bundle responses remain detected.

In various embodiments, the circuit of the IMD 104, including its various embodiments and elements discussed in this document, can be implemented using a combination of hardware and software (including firmware). In various embodiments, the control circuit 224, including its various embodiments and elements discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. In various examples, the control circuit 224, including its various embodiments and elements discussed in this document, can be programmed to perform the various methods discussed in this document.

Figure 3:
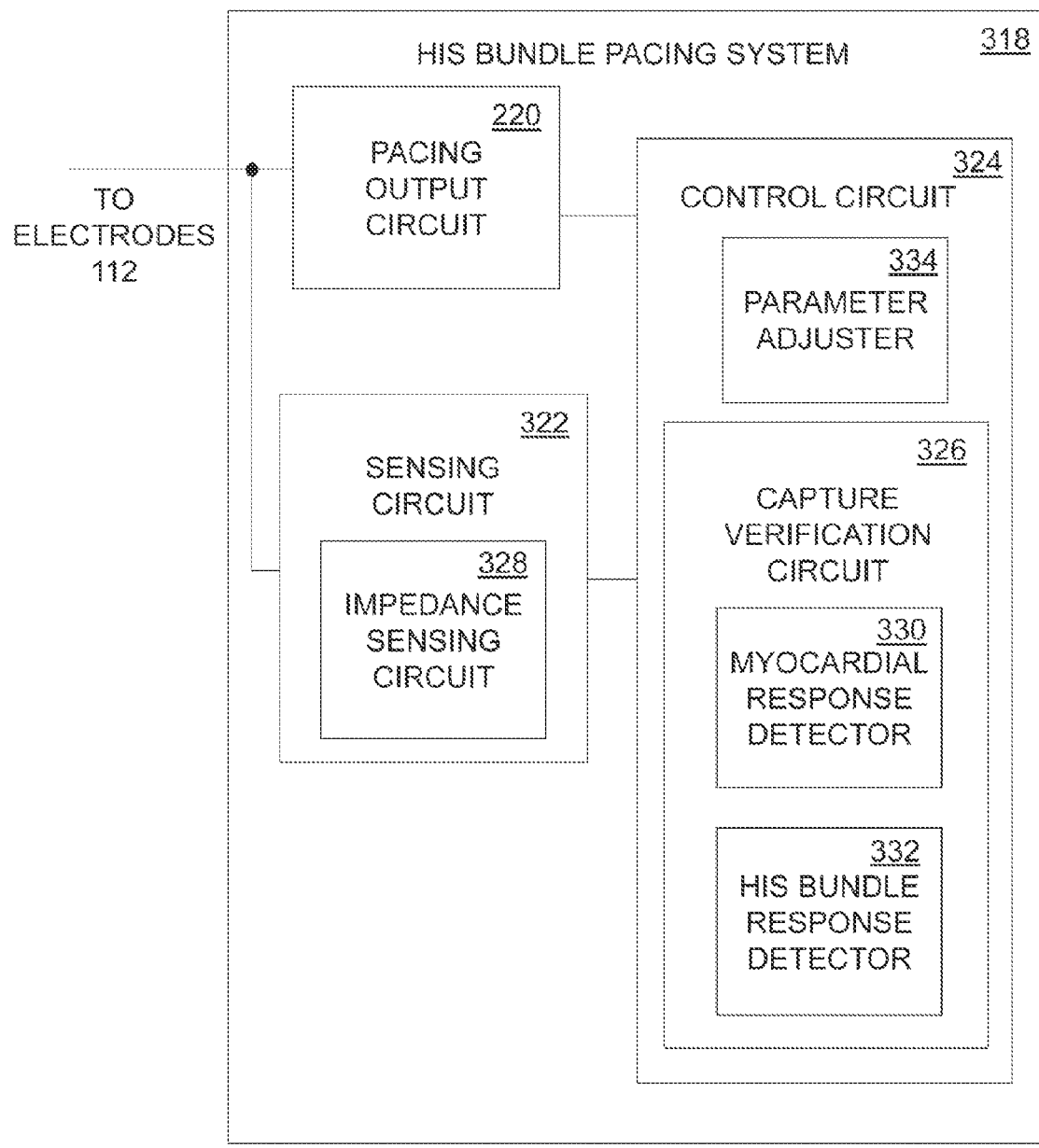
FIG. 3 is a block diagram illustrating another embodiment of the His bundle pacing system.

FIG. 3 is a block diagram illustrating an embodiment of a His bundle pacing system 318. The His bundle pacing system 318 represents an embodiment of the His bundle pacing system 118 and can include pacing output circuit 220, a sensing circuit 322 and a control circuit 324.

The sensing circuit 322 represents an embodiment of sensing circuit 222 and, in addition to the one and more signals sensed by sensing circuit 222 as discussed above, includes an impedance sensing circuit 328. The impedance sensing circuit 328 can sense a change in impedance of one or more portions of the heart 102 in response to the delivery of each pacing pulse. The impedance change in the heart 102 can be due to cardiac mechanical activities such as contraction or relaxation of the four chambers of the heart 102 caused by the pacing pulses. For example, when the His bundle pacing system 318 is electrically coupled to the electrode 112 placed in or on the His bundle 114, the impedance sensing circuit 302 senses an impedance signal that indicates the His bundle responses and the myocardial responses, thereby allowing for the selective His bundle capture verification. In one embodiment, the impedance sensing circuit 302 is configured to sense the impedance signal using the same electrode 112 that can be used for delivering the one or more pacing pulses to the one or more portions of the heart 102. In other words, the His bundle pacing system 318 can be configured to deliver the pacing pulses and sense the impedance signal using one or more common electrodes placed in or on the His bundle 114 of the heart 102. In one embodiment, the His bundle pacing system 318 can be configured to deliver the pacing pulses and sense the impedance signal with different configurations of the electrodes 112. For example, the pacing pulses can be delivering using a bipolar electrode configuration while the impedance signal can be sensed using a unipolar electrode configuration.

The control circuit 324 represents an embodiment of the control circuit 224 and includes a parameter adjuster 334 and a capture verification circuit 326. The capture verification circuit 326 represents an embodiment of the capture verification circuit 226 and is configured to determine the presence or absence of selective His bundle capture using the impedance signal. The capture verification circuit 326 can include a myocardial response detector 330 and a His bundle response detector 332. The myocardial response detector 330 detects the myocardial responses. The His bundle response detector 332 detects the His bundle responses. The capture verification circuit 326 is configured to perform the selective His bundle capture verification based on whether the myocardial responses and the His bundle responses are detected. In one embodiment, the capture verification circuit 326 can be configured to perform the selective His bundle capture verification in response to a user command. In one embodiment, the capture verification circuit 326 can be configured to perform the selective His bundle capture verification according to a specified schedule. For example, the capture verification circuit 326 can be configured to perform the selective His bundle capture verification on a periodic basis. In one embodiment, the capture verification circuit 326 can be configured to perform the selective His bundle capture verification during implantation of the 104.

In one embodiment, the myocardial response detector 330 can be configured to monitor the impedance signal within a detection window to detect one or more of the myocardial responses within the detection window. In one embodiment, the detection window starts from a delivery of the pacing pulse to the His bundle 114 and ends after a specified duration. In one embodiment, the myocardial response detector 330 can be configured to modify the specified duration. In one embodiment, the myocardial response detector 330 is configured to modify the specified duration and/or other timing parameter associated with the detection window in response to a request from the user. In one embodiment, the myocardial response detector 330 can be configured to automatically modify the specified duration and/or other timing parameter associated with the detection window based on sensed or programmed parameters.

The myocardial response detector 330 is configured to detect a cardiac response to a pacing pulse that represents the myocardial response directly caused by the pacing pulse and is distinguishable from the His bundle response directly caused by the pacing pulse. In various embodiments, this cardiac response includes a transient event in the impedance signal sensed within the detection window by the impedance sensing circuit 328. Thus, the myocardial response detector 330 is configured to monitor the impedance signal to detect the transient event in the impedance signal. As discussed above, each of the myocardial responses represents unintentional excitation of portions of the myocardial tissue directly resulting from the delivery of a pacing pulse to the His bundle 114. Therefore, the presence of the transient event within the detection window indicates that the non-selective His bundle pacing has occurred, while the absence of the transient event within the detection window indicates that the selective His bundle pacing has occurred. The duration of the detection window is determined such that the transient event is expected to fall within it while the His bundle response resulting from the same pacing pulse does not fall within it. In one embodiment, the duration of the detection window is determined by measuring the time interval between the transient event and the pacing pulse causing it in a patient population. Accordingly, the duration of the detection window can be set to a value that covers a statistically derived range of the time intervals.

It is noted that the transient event represents the myocardial response including the mechanical response of the myocardium directly caused by the pacing pulse (rather than through the electrical conduction system). While the transient event in the sensed impedance signal is discussed as a specific example, the myocardial response can also be detected as a transient event in one or more other sensed signals that indicate the mechanical response of the myocardium. Thus, in various embodiments, sensing circuit 222 may be configured to sense any one or more signals indicative of the mechanical response of the myocardium directly caused by the pacing pulse, and the myocardial response detector 330 may be configured to monitor such one or more signals to detect the mechanical response. In one embodiment, the myocardial response detector 330 is configured to monitor such a non-impedance signal to detect the mechanical response as a transient event using a technique substantially identical or similar to the technique discussed below for detecting the myocardial responses using the impedance signal.

In one embodiment, the myocardial response detector 330 is configured to measure amplitude of the impedance signal within the detection window and detect the transient event (i.e., one of the myocardial responses) using the measured amplitude of the impedance signal. For example, a presence of the transient event can be established when at any time during the detection window, the measured amplitude of the impedance signal crosses a threshold amplitude. Thus, the myocardial response detector 330 can be configured to compare the measured amplitude of the impedance signal to the threshold amplitude to determine the presence of transient event within the detection window. For example, the myocardial response detector 330 declares that the transient event is detected in response to the measured amplitude of the impedance signal exceeding the threshold amplitude.

In one embodiment, the myocardial response detector 330 is configured to measure a slope of the impedance signal within the detection window and detect the transient event using the measured slope of the impedance signal. In other words, the myocardial response detector 330 is configured to measure a rate of change of the amplitude of the impedance signal within the detection window. For example, a presence of the transient event can be established when at any time during the detection window, the measured slope of the impedance signal crosses a threshold slope. Thus, the myocardial response detector 330 can be configured to compare the measured slope of the impedance signal to the threshold slope to determine the presence of transient event within the detection window. For example, the myocardial response detector 330 declares that the transient event is detected in response to the measured slope of the impedance signal exceeding the threshold slope. In various embodiments, because the measured slope of the impedance signal can be negative or positive, the "measured slope" as discussed above includes an absolute value of the slope.

In one embodiment, the myocardial response detector 330 is configured to measure duration of the impedance signal within the detection window and detect the transient event using the measured duration of the impedance signal. For example, a presence of the transient event can be established when at any time during the detection window, the measured duration of the impedance signal crosses a threshold duration. Thus, the myocardial response detector 330 can be configured to compare the measured duration of the impedance signal with the threshold duration to determine the presence of transient event within the detection window. In various embodiments, the duration of the impedance signal can be measured as a time interval during which the measured amplitude of the impedance signal exceeds a threshold value.

In one embodiment, the His bundle response detector 332 is configured to detect the His bundle responses using the impedance signal. In various embodiments, the capture verification circuit 326 is configured to time the detection windows such that the myocardial responses (the transient events) are each expected to fall within one of the detection windows while the His bundle responses do not fall within the detection windows. This facilitates detection of both the myocardial responses and the His bundle responses using the same impedance signal. For example, a presence of the His bundle response can be established when the measured amplitude of the impedance signal crosses a threshold amplitude after expiration of the detection window. Thus, the His bundle response detector 332 can be configured to compare the measured amplitude of the impedance signal to the threshold amplitude to determine the presence the His bundle response after the expiration of the detection window. For example, the His bundle response detector 332 declares that His bundle response is detected in response to the measured amplitude of the impedance signal exceeding the threshold amplitude. In various embodiments, the threshold amplitudes for detecting the His bundle responses and the myocardial responses can be set independently and can be identical or different, as determined using the patient population for example. In various embodiments, the capture verification circuit 326 can be configured to time the another detection window, during which one of the His bundle response is expected, that follows the detection window for the myocardial response. The duration of this additional detection window may also be determined based on measurements performed using the patient population.

In various embodiments, the parameter adjuster 334 can be configured to adjust one or more pacing parameters in response to a detection of the transient event in the impedance signal. Examples of the one or more pacing parameters adjustable by the parameter adjuster 334 for the purpose of achieving the selective His bundle pacing include pulse amplitude, pulse width, waveform of each pacing pulse, and electrode configuration. In various embodiments, the electrode configuration specifies electrodes to be selected for delivering the pacing pulses. The pacing parameters control the delivery of the pacing pulses from pacing output circuit 220. In one embodiment, the parameter adjuster 334 can be configured to adjust the one or more pacing parameters such that no myocardial response (the transient event) is detected by the myocardial response detector 330, an as to achieve the selective His bundle pacing. In another embodiment, the parameter adjuster 334 can be configured to adjust the one or more pacing parameters such that the His bundle responses are detected by the His bundle detector 332 while no myocardial response (the transient event) is detected by the myocardial response detector 330, so as to achieve the selective His bundle pacing.

It has been observed that the selective His bundle pacing is associated with a latency period between the delivery of a pacing pulse to the His bundle 114 and mechanical activation of the targeted portion (i.e., His bundle 114) of the heart 102 as indicated by the impedance signal. This latency period is the time interval between the delivery of a pacing pulse to the His bundle response resulting from the delivery of that pacing pulse. An absence or substantial shortening of the latency period indicates that the myocardial response is present. The myocardial response includes mechanical activation of one or more non-targeted portions of the heart 102. Thus, in various embodiments, the parameter adjuster 334 can be configured to adjust the pacing parameters such that the latency period within an expected normal range of length is observed and/or detected.

In various embodiments, the control circuit 324 can be configured to continuously control the delivery of the pacing pulses from pacing output circuit 220 using an outcome of the selective His bundle capture verification performed by the capture verification circuit 326. In response to the myocardial responses being detected from the impedance signal within the detection windows, the parameter adjuster 334 adjusts one or more pacing parameters controlling the delivery of the pacing pulses such that the myocardial responses are longer detected. In response to His bundle pacing not being detected, the parameter adjuster 334 adjusts one or more pacing parameters controlling the delivery of the pacing pulses to ensure His bundle capture. Thus, the parameter adjuster 334 can be configured to adjust one or more pacing parameters to achieve the selective His bundle pacing, for which the His bundle responses are detected while the myocardial responses are not detected.

Figure 4:
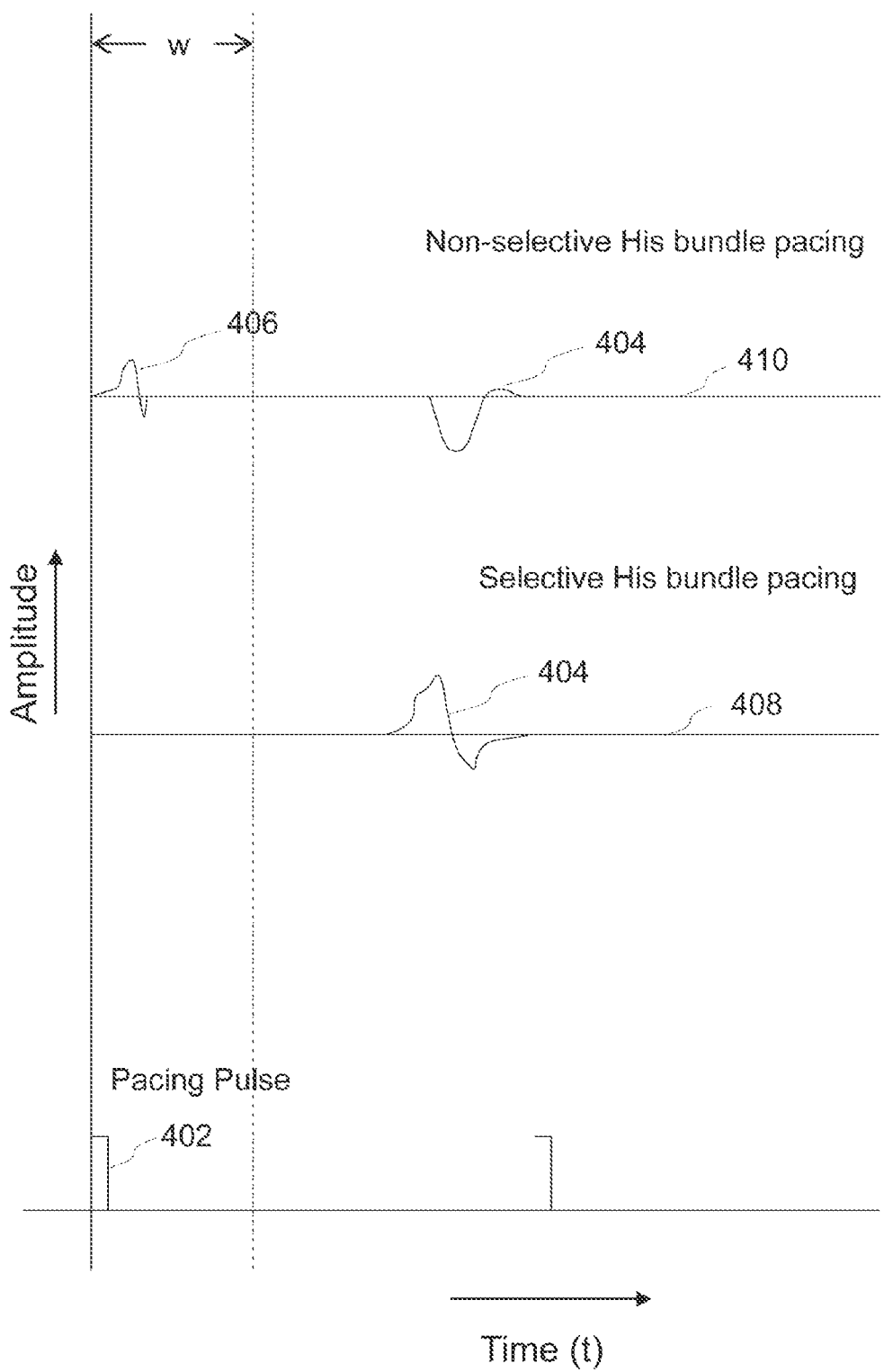
FIG. 4 is a diagram illustrating an example of cardiac events following delivery of a pacing puke to the His Bundle.

FIG. 4 is a diagram illustrating an example of cardiac events following delivery of a pacing pulse to the His Bundle 114. As shown in the FIG. 4, the signal 402 represents the pacing pulse. The pacing pulse can result in the selective or the non-selective His bundle pacing. A signal 410 illustrates the non-selective His bundle pacing in which the pacing pulse 402 results in a His bundle capture 404 as well as the myocardial response (the transient event) 406. A signal 408 illustrates the selective His bundle pacing in which the pacing pulse 402 results in a His bundle capture 404 without also resulting in the myocardial response (the transient event) 406. The myocardial response 406 is expected to occur during the detection window (W). The latency period as discussed above refers to the time interval between the pacing pulse 402 and the His bundle capture 404 as seen in the signal 408. In the signal 410, this latency period is eliminated or substantially shortened by the presence of the myocardial response 406.

Figure 5:
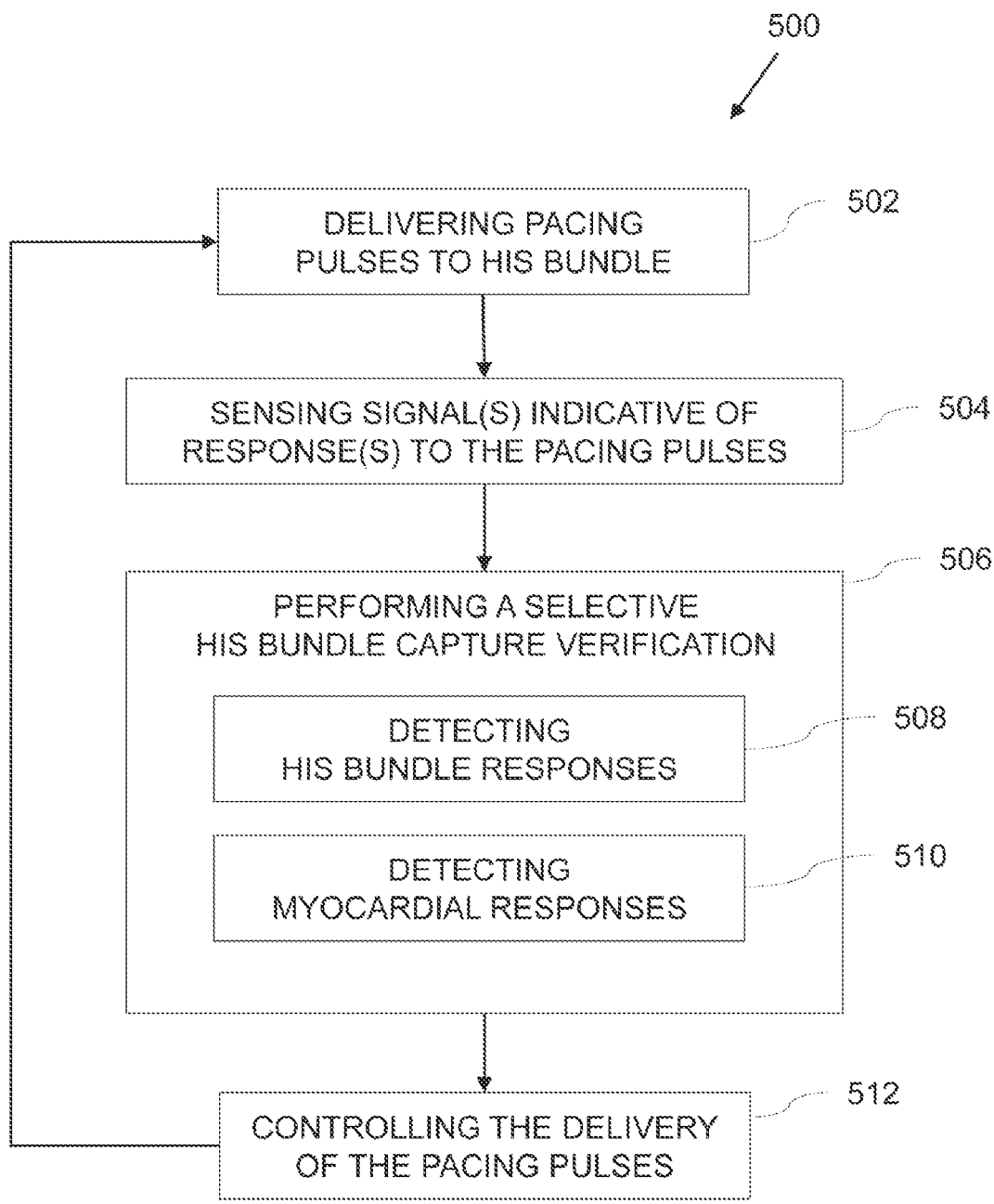
FIG. 5 is a flow chart illustrating an embodiment of a method for operating an implantable cardiac pacemaker.

FIG. 5 is a flow chart illustrating an embodiment of a method 500 for operating an implantable cardiac pacemaker. In one embodiment, the method 500 is performed using system 100, including the various embodiments of its elements as discussed in this document. In various embodiments, the method 500, including its various embodiments, can also be performed for the selective pacing of a branch of the electrical conduction system of the heart other than the His bundle. In other words, the His bundle is discussed as a specific example in which the method 500, including its various embodiments, can be applied.

At 502, pacing pulses are delivered to the His bundle of a heart. The delivery of the pacing pulses may result in the selective His bundle pacing or the non-selective His bundle pacing as discussed above. At 504, one or more signals indicative of one or more responses of the heart 102 to the delivery of each pulse of the pacing pulses are sensed. Examples of the one or more signals include electrogram, impedance signals, and any other signal(s) allowing for determining whether a pacing pulse results in the selective or non-selective His bundle pacing. At 506, a selective His bundle capture verification is performed using the sensed one or more signals. In one embodiment, the selective His bundle capture verification is repeatedly performed according to a specified schedule. For example, the selective His bundle capture verification can be performed on a periodic basis. In one embodiment, the selective His bundle capture verification is performed during implantation of the cardiac pacemaker. In one embodiment, the selective His bundle capture verification is performed in response to a user command communicated to the cardiac pacemaker via telemetry.

The process of the selective His bundle capture verification includes detection of His bundle responses and myocardial responses. As discussed above, the His bundle responses are each representative of an excitation of the His bundle directly resulting from the delivery of one of the pacing pulses, and the myocardial responses are each representative of an unintended and undesirable excitation of myocardial tissue, particularly myocardial tissue adjacent to the His bundle, directly resulting from the delivery of one of the pacing pulses. At 508, His bundle responses are detected. At 510, myocardial responses are detected.

At 512, the delivery of the pacing pulses to the His bundle is controlled using an outcome of the selective His bundle capture verification. In various embodiments, this can include adjustment of one or more pacing parameters such as purse amplitude, pulse width, waveform of the pacing pulses, and electrode configuration. The electrode configuration parameter specifies electrodes selected for delivering the pacing pulses to a specified target cite such that the His bundle. In one example, the selective His bundle pacing may be achieved by adjusting the target site to which the pacing pulses are delivered, and the target site is programmable by programming the electrode configuration. In another example, the selective His bundle pacing may be achieved by selecting the electrode configuration from a bipolar electrode configuration and a unipolar electrode configuration, and the selection is made by programming the electrode configuration.

Figure 6:
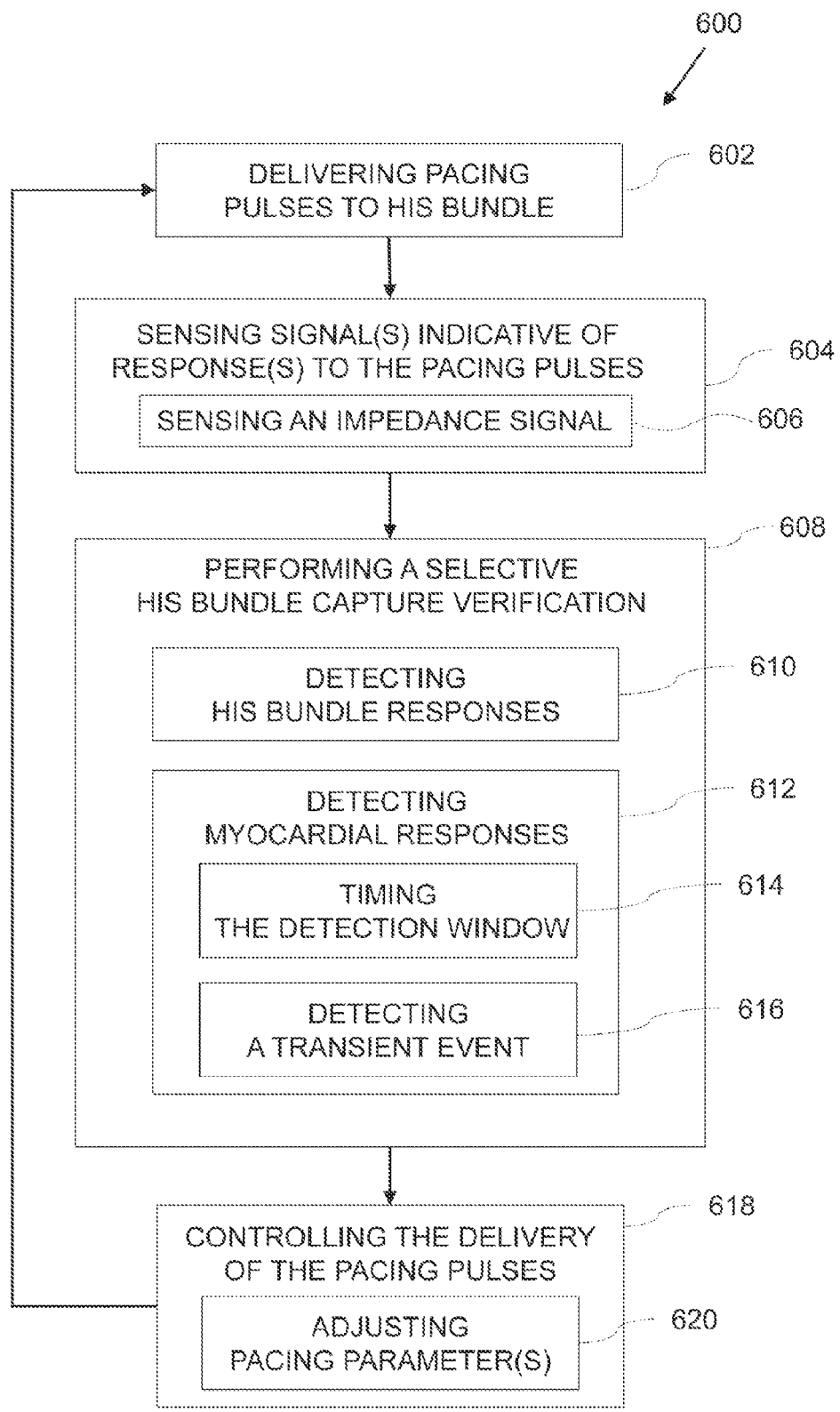
FIG. 6 is a flow chart illustrating an embodiment of a method for operating an implantable cardiac pacemaker configured to perform a selective His bundle capture verification using an impedance signal.

FIG. 6 is a flow chart illustrating an example of a method 600 for operating an implantable cardiac pacemaker for the selective His bundle pacing. The method 600 represents an embodiment of the method 500. In one embodiment, the method 600 is performed using system 100, including the various embodiments of its elements as discussed in this document.

At 602, the pacing pulses are delivered to the His bundle. At 604, one or more signals indicative of one or more responses of the heart 102 to the delivery of each pulse of the pacing pulses are sensed. In one embodiment, an impedance signal is sensed as one of the one or more signals at 606. The impedance signal is indicative of responses of various portions of the heart to the delivery of each pulse of the pacing pulses.

At 608, the selective His bundle capture verification is performed. In various embodiments, the selective His bundle capture verification can be performed according to a specified schedule such as on a periodic basis, during implantation of the cardiac pacemaker, and/or in response to a user command communicated to the cardiac pacemaker via telemetry. The process of the selective His bundle capture verification includes detecting the His bundle responses at 610 and detecting the myocardial responses at 612. In one embodiment, the His bundle responses and the myocardial responses are detected using the impedance signal.

In the illustrated embodiment, the myocardial responses are each detected by timing a detection window at 614 and detecting a transient event within the detection window at 616. The detection window can start from the delivery of each pulse of the pacing purses and has a specified duration. This duration is a time interval during which the transient event (representing the myocardial response) is expected to occur. In one embodiment, the duration is determined statistically based on measurements made using a patient population. The presence if the transient event is an indication of the non-selective His bundle pacing.

At 618, the delivery of the pacing pulses to the His bundle is controlled using an outcome of the selective His bundle capture verification. In the illustrated embodiment, this includes adjusting the one or more pacing parameters controlling the delivery of the pacing pulses at 620. In one embodiment, the one or more pacing parameters are adjusted such that no myocardial response (the transient event) is detected, so as to achieve the selective His bundle pacing. In another embodiment, the one or more pacing parameters are adjusted such that the His bundle responses are detected while no myocardial response (the transient event) is detected, so as to achieve the selective His bundle pacing.

Figure 7:
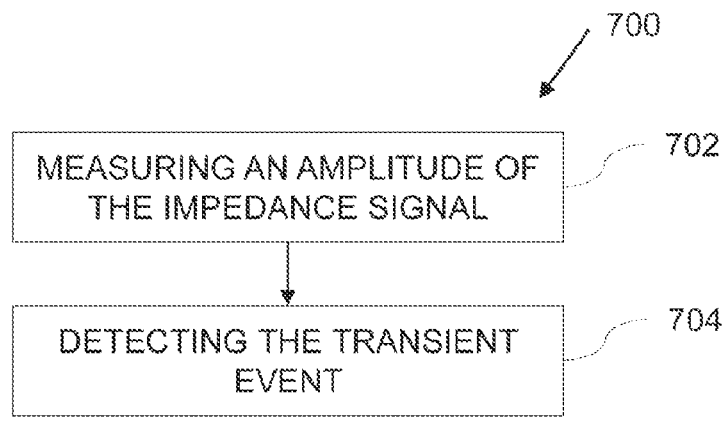
FIG. 7 is a diagram illustrating an embodiment of a method for detecting a transient event using amplitude of the impedance signal.

FIG. 7 is a diagram illustrating an example of a method 700 for detecting the transient event using amplitude of the impedance signal. The method 700 represents an embodiment of step 616 of the method 600. In one embodiment, the method 700 is performed by myocardial response detector 330.

At 702, the amplitude of the impedance signal is measured. At 704, the transient event is detected using the measured amplitude of the impedance signal. In one embodiment, a presence of the transient event can be established when at any time during the detection window, the measured amplitude of the impedance signal crosses a threshold amplitude. For example, the transient event is detected in response to the measured amplitude of the impedance signal exceeding the threshold amplitude.

Figure 8:
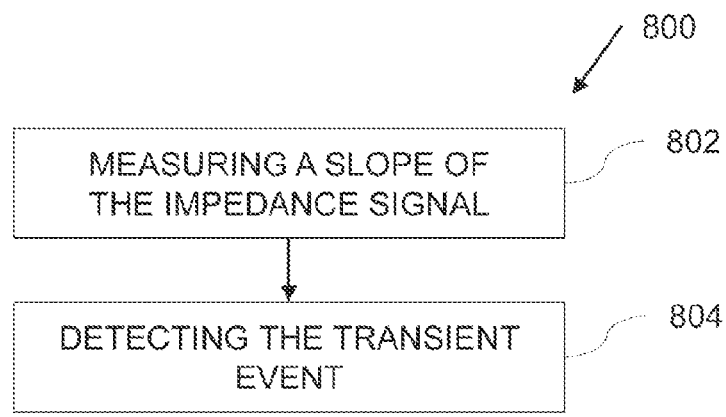
FIG. 8 is a diagram illustrating an embodiment of a method for detecting a transient event using slope of the impedance signal.

FIG. 8 is a diagram illustrating an embodiment of a method 800 for detecting a transient event using slope of the impedance signal. The method 800 represents another embodiment of step 616 of the method 600. In one embodiment, the method 800 is performed by myocardial response detector 330.

At 802, the slope of the impedance signal is measured. In one embodiment, because the slope can be positive or negative, its absolute value is used as the measured slope of the impedance signal. At 804, the transient event is detected using the measured slope of the impedance signal. In one embodiment, a presence of the transient event can be established when at any time during the detection window, the measured slope of the impedance signal crosses a threshold slope. For example, the transient event is detected in response to the measured slope of the impedance signal exceeding the threshold slope.

Figure 9:
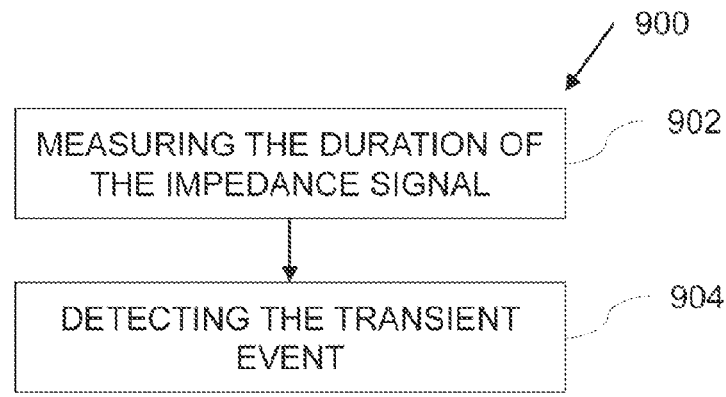
FIG. 9 is a diagram illustrating an embodiment of a method for detecting a transient event using duration of the impedance signal.

FIG. 9 is a diagram illustrating an embodiment of a method 900 for detecting a transient event using duration of the impedance signal. The method 900 represents another embodiment of step 616 of the method 600. In one embodiment, the method 900 is performed by myocardial response detector 330.

At 902, the duration of the impedance signal is measured. In one embodiment, the duration is measured as the time interval during which the amplitude of the impedance signal exceeds a specified threshold. At 904 the transient event is detected using the measured duration of the impedance signal. In one embodiment, a presence of the transient event can be established when at any time during the detection window, the measured duration of the impedance signal crosses a threshold duration. For example, the transient event is detected in response to the measured duration of the impedance signal exceeding the threshold duration.

In various embodiments, each of the methods 700, 800, and 900 can also be applied to detect the His bundle response for verification of capture of the His bundle using the impedance signal. For example, the method 700 can be applied to detect the His bundle response and declare capture of the His bundle in response to the measured amplitude of the impedance signal exceeding a threshold amplitude determined for the His bundle response. The method 800 can be applied to detect the His bundle response and declare capture of the His bundle in response to the measured amplitude of the impedance signal exceeding a threshold slope determined for the His bundle response. The method 900 can be applied to detect the His bundle response and declare capture of the His bundle in response to the measured duration of the impedance signal exceeding a threshold duration determined for the His bundle response.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for pacing a heart having conduction tissue including a His bundle and myocardial tissue, comprising:
 a pacing output circuit configured to deliver cardiac pacing pulses to a target portion of the conductive tissue;
 a sensing circuit configured to sense one or more signals indicative of one or more responses of the heart to the delivery of each pulse of the cardiac pacing pulses; and
 a control circuit coupled to the pacing output circuit and the sensing circuit, the control circuit configured to control the delivery of the cardiac pacing pulses using pacing parameters and including:
  a capture verification circuit configured to perform a selective capture verification including detection of conductive tissue responses and myocardial responses using the sensed one or more signals, the conductive tissue responses each representative of excitation of the target portion of the conductive tissue directly resulting from the delivery of the each pulse, the myocardial responses each representative of excitation of portions of the myocardial tissue directly resulting from the delivery of the each pulse; and
  a parameter adjuster configured to adjust at least one parameter of the pacing parameters using an outcome of the selective capture verification such that the conductive tissue responses are detected and the myocardial responses are not detected.

2. The system of claim 1, wherein the target portion of the conductive tissue is the His bundle, the control circuit is configured to control the delivery of the cardiac pacing pulses to the His bundle using pacing parameters, and the capture verification circuit is configured to perform a selective His bundle capture verification including detection of His bundle responses and myocardial responses using the sensed one or more signals, the His bundle responses each representative of excitation of the His bundle directly resulting from the delivery of the each pulse, the myocardial responses each representative of excitation of portions of the myocardial tissue directly resulting from the delivery of the each pulse.

3. The system of claim 2, wherein the control circuit comprises a parameter adjuster configured to adjust at least a pulse amplitude a pulse width, a pulse waveform, or an electrode configuration of the pacing parameters using an outcome of the selective His bundle capture verification such that the His bundle responses are detected and the myocardial responses are not detected.

4. The system of claim 3, wherein the capture verification circuit is configured to perform the selective His bundle capture verification according to a specified schedule.

5. The system of claim 3, wherein the sensing circuit comprises an impedance sensing circuit configured to sense an impedance signal of the one or more signals, and the capture verification circuit comprises a myocardial response detector configured to detect the myocardial responses each indicated by a transient event in the impedance signal, the transient event indicative of a response of the myocardial responses.

6. The system of claim 5, wherein the capture verification circuit further comprises a His bundle response detector configured to detect the His bundle responses using the impedance signal.

7. The system of claim 5, wherein the myocardial response detector is configured to time detection windows and to detect the transient event during each of the detection windows, the detection windows each starting from the delivery of the each pulse and having a specified duration.

8. The system of claim 7, wherein the myocardial response detector is configured to measure an amplitude of the impedance signal and detect the transient event using the amplitude.

9. The system of claim 7, wherein the myocardial response detector is configured to measure a slope of the impedance signal and detect the transient event using the slope.

10. The system of claim 7, wherein the myocardial response detector is configured to measure a duration of the impedance signal and detect the transient event using the duration.

11. A method for operating an implantable cardiac pacemaker configured to stimulate a heart having conductive tissue including a His bundle and myocardial tissue, comprising:
    delivering cardiac pacing pulses to a target portion of the conductive tissue from the implantable cardiac pacemaker;
    controlling the delivery of the cardiac pacing pulses using pacing parameters;
    sensing one or more signals indicative of one or more responses of the heart to the delivery of each pulse of the cardiac pacing pulses;
    performing a selective capture verification including:
        detecting conductive tissue responses using a first signal of the sensed one or more signals, the conductive tissue responses each representative of excitation of the target portion of the conductive tissue directly resulting from the delivery of the each pulse; and
        detecting myocardial responses using a second signal of the sensed one or more signals, the myocardial responses each representative of excitation of portions of the myocardial tissue directly resulting from the delivery of the each pulse; and
    adjusting at least one parameter of the pacing parameters using an outcome of the selective capture verification such that the conductive tissue responses are detected and the myocardial responses are not detected.

12. The method of claim 11, wherein delivering the cardiac pacing pulses to the target portion of the conductive tissue comprises delivering the cardiac pacing pulses to the His bundle, and performing the selective capture verification comprises performing a selective His bundle capture verification including:
    detecting His bundle responses using the first signal, the His bundle responses each representative of excitation of the His bundle directly resulting from the delivery of the each pulse; and
    detecting the myocardial responses using the second signal.

13. The method of claim 12, comprising adjusting at least a pulse amplitude, a pulse width, a pulse waveform, or an electrode configuration of the pacing parameters using an outcome of the selective His bundle capture verification such that the His bundle responses are detected and the myocardial responses are not detected.

14. The method of claim 13, comprising performing the selective His bundle capture verification upon implantation of the implantable cardiac pacemaker and on a periodic basis.

15. The method of claim 12, wherein sensing the one or more signals comprises sensing an impedance signal, and detecting the myocardial responses comprises:
    timing the detection windows each starting from the delivery attic each pulse and having a specified duration; and
    detecting a transient event in the impedance signal during each detection window of the detection windows, the transient event indicative of a response of the myocardial responses.

16. The method of claim 15, comprising:
    measuring an amplitude of the impedance signal; and
    detecting the transient event using the measured amplitude.

17. The method of claim 15, comprising:
    measuring a slope of the impedance signal; and
    detecting the transient event using the measured slope.

18. The method of claim 15, comprising:
    measuring a duration of the impedance signal; and
    detecting the transient event using the measured duration.

19. The method of claim 15, wherein detecting the His bundle responses comprises detecting the His bundle responses using the impedance signal.

20. The method of claim 15, comprising delivering the cardiac pacing pulses and sensing the impedance signal using at least one common electrode placed in the His bundle.

* * * * *